US008998967B2

(12) United States Patent
Biedermann et al.

(10) Patent No.: US 8,998,967 B2
(45) Date of Patent: *Apr. 7, 2015

(54) RECEIVING PART FOR RECEIVING A ROD FOR COUPLING THE ROD TO A BONE ANCHORING ELEMENT AND A BONE ANCHORING DEVICE WITH SUCH A RECEIVING PART

(71) Applicant: Biedermann Technologies GmbH & Co. KG, Donaueschingen (DE)

(72) Inventors: Lutz Biedermann, VS-Villingen (DE); Wilfried Matthis, Weisweil (DE); Berthold Dannecker, St. Georgen (DE)

(73) Assignee: Biedermann Technologies GmbH & Co. KG, Donaueschingen (DE)

( * ) Notice: Subject to any disclaimer, the term of this patent is extended or adjusted under 35 U.S.C. 154(b) by 0 days.

This patent is subject to a terminal disclaimer.

(21) Appl. No.: 14/147,371

(22) Filed: Jan. 3, 2014

(65) Prior Publication Data

US 2014/0296927 A1 Oct. 2, 2014

Related U.S. Application Data

(63) Continuation of application No. 12/626,830, filed on Nov. 27, 2009, now Pat. No. 8,636,781.

(60) Provisional application No. 61/118,558, filed on Nov. 28, 2008.

(30) Foreign Application Priority Data

Nov. 28, 2008 (EP) ..................................... 08020737

(51) Int. Cl.
*A61B 17/86* (2006.01)
*A61B 17/68* (2006.01)
*A61B 17/70* (2006.01)

(52) U.S. Cl.
CPC ........... *A61B 17/685* (2013.01); *A61B 17/7032* (2013.01); *A61B 17/7037* (2013.01); *A61B 17/7035* (2013.01)

(58) Field of Classification Search
CPC ............... A61B 17/70; A61B 17/7001; A61B 17/7032; A61B 17/7034; A61B 17/7035; A61B 17/7037; A61B 17/86; A61B 17/8605; A61B 17/864; A61B 17/8685
USPC ......... 606/305–308, 319, 328, 279, 266–270, 606/272
See application file for complete search history.

(56) References Cited

U.S. PATENT DOCUMENTS

| 4,946,458 A | 8/1990 | Harms et al. |
| 5,443,467 A | 8/1995 | Biedermann et al. |

(Continued)

FOREIGN PATENT DOCUMENTS

| EP | 2022423 A1 | 2/2009 |
| KR | 2000-0048562 A | 7/2000 |

(Continued)

OTHER PUBLICATIONS

Korean Notice of Allowance for Application No. KR 10-2009-0113970, dated Jan. 30, 2015, and English translation (6 pages).

*Primary Examiner* — Eduardo C Robert
*Assistant Examiner* — Julianna N Harvey
(74) *Attorney, Agent, or Firm* — Christie, Parker & Hale, LLP

(57) ABSTRACT

A receiving part for receiving a rod for coupling the rod to a bone anchoring element includes a receiving part body including a rod receiving portion with a channel for receiving a rod, and a head receiving portion for accommodating a head of a bone anchoring element, the head receiving portion having an open end and being flexible so as to allow introduction and clamping of the head, the head receiving portion having an exterior surface with a tapered portion; and a locking ring around the head receiving portion and including an interior surface with a curved portion configured to engage the tapered portion of the exterior surface of the head receiving portion to clamp the head.

20 Claims, 7 Drawing Sheets

(56) References Cited

U.S. PATENT DOCUMENTS

| | | | |
|---|---|---|---|
| 5,549,608 | A | 8/1996 | Errico et al. |
| 5,672,179 | A | 9/1997 | Garth et al. |
| 5,728,098 | A * | 3/1998 | Sherman et al. ............. 606/269 |
| 5,733,285 | A | 3/1998 | Errico et al. |
| 6,063,090 | A | 5/2000 | Schläpfer |
| 6,254,602 | B1 | 7/2001 | Justis |
| 7,445,627 | B2 | 11/2008 | Hawkes et al. |
| 2001/0047173 | A1 | 11/2001 | Schlapfer et al. |
| 2003/0023240 | A1 | 1/2003 | Amrein et al. |
| 2005/0080415 | A1* | 4/2005 | Keyer et al. ..................... 606/61 |
| 2005/0096653 | A1 | 5/2005 | Doubler et al. |
| 2005/0228385 | A1 | 10/2005 | Iott et al. |
| 2005/0228392 | A1* | 10/2005 | Keyer et al. ..................... 606/86 |
| 2006/0004357 | A1 | 1/2006 | Lee et al. |
| 2006/0084978 | A1 | 4/2006 | Mokhtar |
| 2006/0129149 | A1 | 6/2006 | Iott et al. |
| 2006/0200128 | A1* | 9/2006 | Mueller .......................... 606/61 |
| 2006/0241599 | A1 | 10/2006 | Konieczynski et al. |
| 2006/0247624 | A1 | 11/2006 | Banouskou et al. |
| 2006/0271047 | A1 | 11/2006 | Jackson |
| 2008/0009862 | A1 | 1/2008 | Hoffman |
| 2008/0161859 | A1 | 7/2008 | Nilsson |
| 2008/0243193 | A1 | 10/2008 | Ensign et al. |
| 2008/0269742 | A1 | 10/2008 | Levy et al. |
| 2008/0312696 | A1 | 12/2008 | Butters et al. |
| 2008/0312697 | A1 | 12/2008 | Butters et al. |
| 2008/0312701 | A1 | 12/2008 | Butters et al. |
| 2009/0149887 | A1* | 6/2009 | Schlaepfer et al. ........... 606/278 |

FOREIGN PATENT DOCUMENTS

| | | |
|---|---|---|
| KR | 10-2008-0014802 A | 2/2008 |
| KR | 10-2008-0042863 A | 5/2008 |
| WO | WO 98/12977 A1 | 4/1998 |
| WO | WO 2004/089245 A2 | 10/2004 |
| WO | WO 2005/041821 A2 | 5/2005 |
| WO | WO 2006/119241 A2 | 11/2006 |
| WO | WO 2007/019060 A1 | 2/2007 |
| WO | WO 2007/038350 A2 | 4/2007 |

* cited by examiner

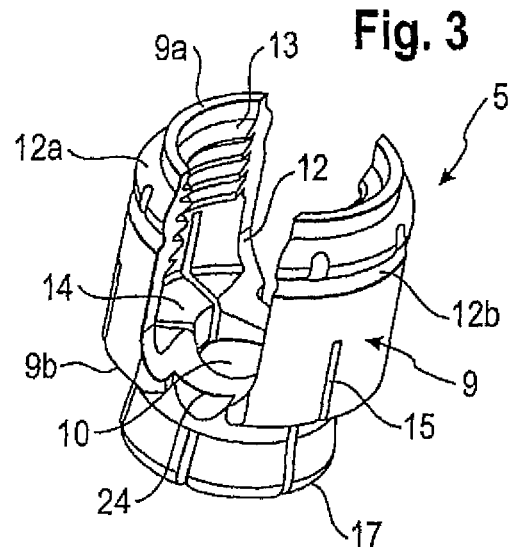
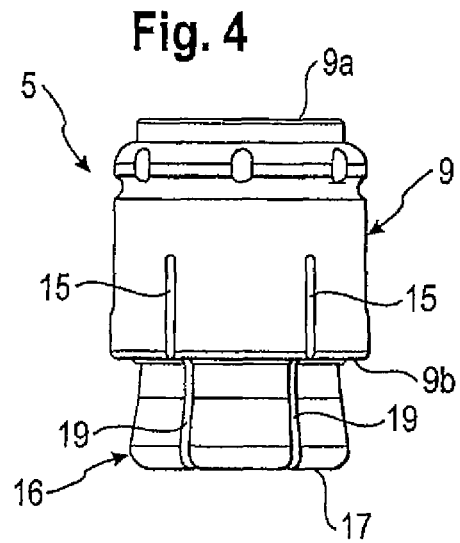
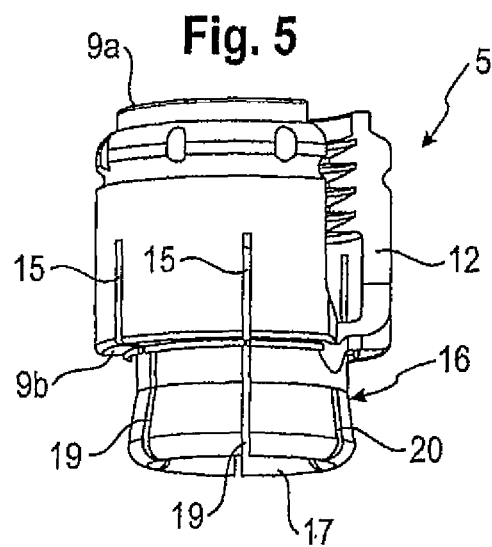
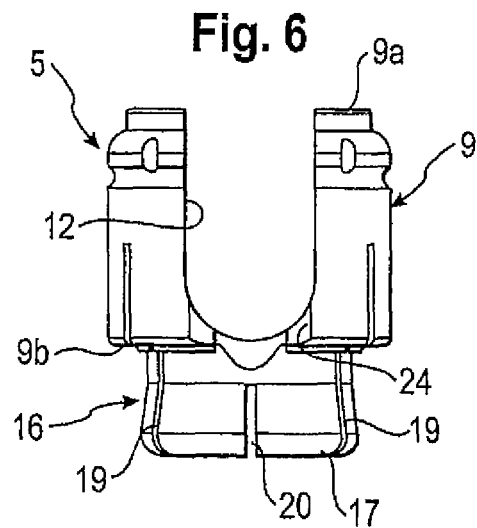
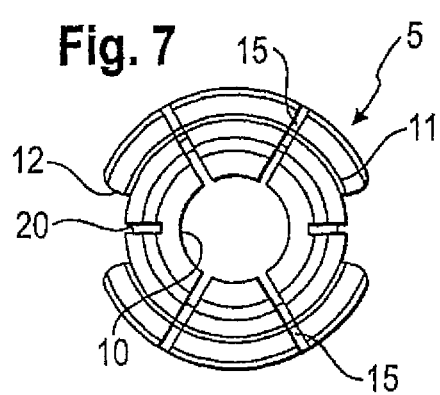
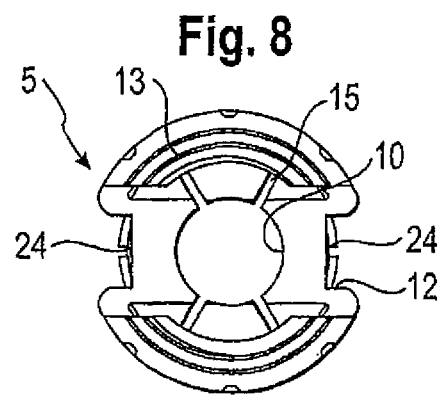

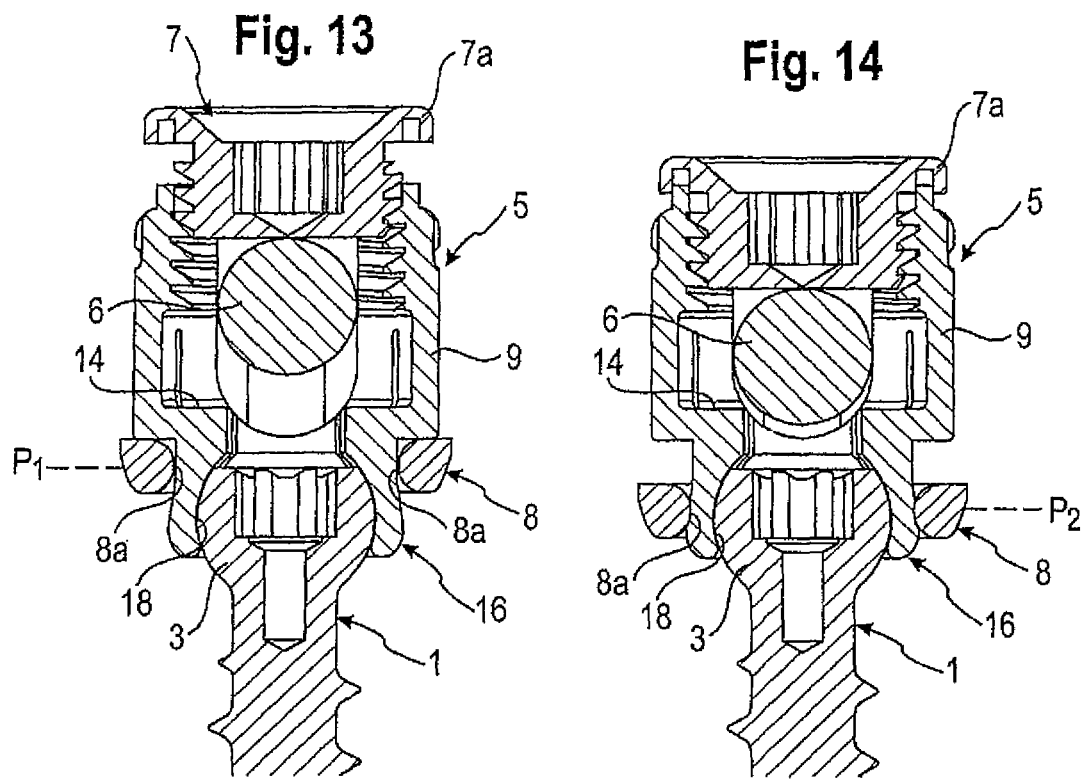
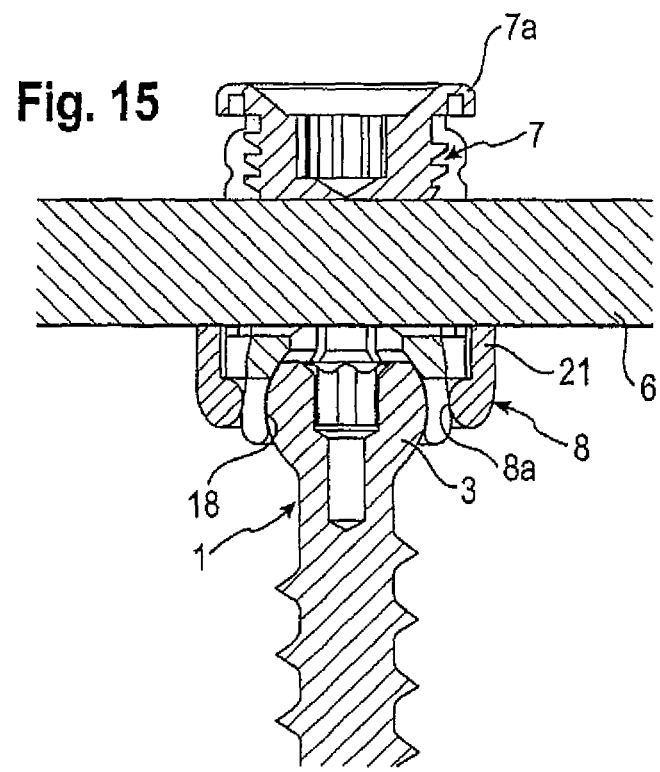

RECEIVING PART FOR RECEIVING A ROD FOR COUPLING THE ROD TO A BONE ANCHORING ELEMENT AND A BONE ANCHORING DEVICE WITH SUCH A RECEIVING PART

CROSS-REFERENCE TO RELATED APPLICATION

This application is a continuation of U.S. patent application Ser. No. 12/626,830, filed Nov. 27, 2009, which claims priority to and the benefit of U.S. Provisional Patent Application Ser. No. 61/118,558, filed Nov. 28, 2008, the contents of which are hereby incorporated by reference in their entirety, and claims priority from European Patent Application EP 08 020 737.6, filed Nov. 28, 2008, the contents of which are hereby incorporated by reference in their entirety.

BACKGROUND

1. Field

The invention relates to a receiving part for receiving a rod for coupling the rod to a bone anchoring element and a bone anchoring device with such a receiving part. The head of the bone anchoring element is locked in the receiving part by compression of a head receiving portion of the receiving part laterally surrounding the head by means of a locking ring. The head receiving portion of the receiving part has an exterior surface with a tapered portion and the locking ring has an interior surface with a curved portion which presses against the tapered portion of the exterior surface of the head receiving portion to compress the head receiving portion to clamp the head. The bone anchoring device can be realized, for example, in the form of a polyaxial bone screw allowing a pivotal movement of the head.

2. Description of Related Art

Various designs of polyaxial bone screws are known wherein each design has particular characteristics and wherein different locking principles are used.

U.S. Pat. No. 5,443,467 describes a polyaxial bone screw having a screw element and a receiving part and a pressure element acting onto the head of the screw element to press it down against the seat in the receiving part in order to lock the rotational position of the head. A bone screw usually is pre-assembled so that the screw element is screwed into the bone with a receiving part mounted on the screw element.

Other bone screws are known wherein the head is clamped from the side to lock the rotational position.

U.S. Pat. No. 4,946,458 describes a bone screw with a receiving part consisting of two spherically-shaped halves pressing from two lateral sides onto the spherical head. The halves are held together in their lower portion by a ring.

U.S. Pat. No. 5,672,179 describes a bone screw with a receiving part with a conically shaped seat and a conically shaped pressure element which exerts pressure onto the head from above and from the side. If the cone angle has a value lying within a specific range self-locking of the pressure element within the receiving part takes place which allows to preliminary lock the head within the receiving part while the rod is still movable in order to allow the adjustment of its position.

U.S. Pat. No. 6,063,090 A describes a bone screw with a receiving part having a conically-shaped cavity accommodating the head wherein a spring chuck is provided in the cavity which is downwardly and radially compressible to clamp the head. With this bone screw it is possible to click the receiving part onto the head of the screw element which allows to screw the screw element into the bone and to connect it to the receiving part thereafter.

U.S. Pat. No. 5,728,098 describes a bone screw for connection to a spinal rod comprising a screw element and a receiver member which has slits provided at the bottom of the rod receiving channel and wherein two ring shaped compression members made of a shape-memory alloy are provided at the lower side and the upper side of the receiver member, respectively. The compression members contract about the portions of the receiver member when the temperature is elevated so that the rod is clamped in the channel.

U.S. Pat. No. 5,549,608 describes a polyaxial bone screw with a screw element with a spherical head and a coupling element to couple the screw element into a spinal rod. The coupling element has a tapered lower portion including a slotted interior chamber in which the spherical head is initially polyaxially disposed. The coupling element further comprises a recess for receiving the head. In addition, a locking ring surrounding the lower portion of the coupling element and a cylindrical rod securing sleeve which fits over the coupling element are provided. A top locking nut is used to exert pressure onto the rod securing sleeve. The head is locked in the interior chamber by means of the locking ring which is pressed down by the rod securing sleeve.

U.S. Pat. No. 5,733,285 describes a similar polyaxial bone screw wherein in one embodiment the rod securing sleeve is omitted and the rod directly presses onto a locking collar disposed around the tapered and colleted portion of the coupling element. The locking collar has to be placed onto the coupling element from above. It is not secured against escaping towards the upper end and against rotation when the rod is not inserted. Furthermore, the size of the known bone anchoring device is quite large as the locking collar and the top locking nut extend substantially outward from the diameter of the coupling element.

WO 2007/038350 A2 discloses an apparatus for connecting a bone anchor to a support rod including a connector body and a cap. The connector body has a socket for insertion, angulation and removal a bone anchor, the socket having a section with a spherical outer surface. A sleeve is provided which is configured to fit over the connector body, the sleeve having a conical inside wall which is tangential to the spherical outer surface of the spherical section. The contact between the spherical section and the conical inside wall occurs around an annulus defining a circular contact zone. This circular contact zone provides uniform compression of the chamber receiving the bone anchor by the sleeve. The sleeve extends over the whole length of the socket.

US 2005/0080415 A1 describes a polyaxial bone anchor for attaching a rod to a bone comprising an anchor member and a body member having a U-shaped channel for receiving the rod and a compressible recess for receiving a head of the anchor member. A portion of an exterior surface of the compressible recess is tapered and a collar is slidably disposed about the body member. The collar comprises an interior surface portion which is tapered and which cooperates with the tapered exterior surface portion of the compressible recess.

SUMMARY

It is the object of the invention to provide an improved receiving part for receiving a rod for coupling the rod to a bone anchoring element and a bone anchoring device with such a receiving part, which has a small size while simultaneously providing a safe locking and which can be used as a modular system.

The bone anchoring device according to an embodiment of the invention comprises few elements, which reduces the costs of manufacturing and which facilitates handling. It makes use of the principle of clamping the head of the bone anchoring element circumferentially from the lateral sides which reduces the force necessary to safely clamp the head. The design of the bone anchoring device allows to further reduce the dimension in terms of height as well as in terms of the bottom outer diameter which is particularly suitable for applications where small-sized anchoring devices are utilized, such as in the field of cervical spinal surgery or pediatric applications, trauma and minimally invasive applications.

The head of the bone anchoring element can be inserted into the receiving part at any time before or during surgery. Therefore, it is, for example, possible to first anchor the bone anchoring element in the bone and thereafter connect it to the receiving part and the rod. By providing various bone anchors with different receiving parts a modular system is available prior to surgery.

Since the height of the locking ring is smaller than the height of the head receiving portion the receiving part has a profile with a small diameter. In one embodiment, the pressure exerted via the locking ring onto the head receiving portion is largest at a position of the largest diameter of the head of the bone anchoring element. Therefore, the locking ring does not have to extend up to the open end of the head receiving portion which allows for a locking ring with a reduced diameter.

The locking ring is moveable between a position in which the head is not clamped and a position in which the head is locked. The locking ring can be releasably held in either of the two end positions which makes handling very convenient.

Since the locking ring has a curved interior surface portion, jamming between the locking ring and the head receiving portion does not occur.

BRIEF DESCRIPTION OF THE DRAWINGS

Further features and advantages of the invention will become apparent from the description of embodiments using the accompanying drawings. In the drawings:

FIG. 3 shows a perspective view of the receiving part according to the first embodiment.

FIG. 4 shows a side view of the receiving part of FIG. 3.

FIG. 5 shows another perspective view of the receiving part of FIG. 3.

FIG. 6 shows a side view of the receiving part of FIG. 4 rotated by 90°.

FIG. 7 shows a bottom view of the receiving part of FIG. 3.

FIG. 8 shows a top view of the receiving part of FIG. 3.

FIG. 13 shows a sectional view of the bone anchoring device according to the first embodiment in a first position of the locking ring, the section being taken perpendicular to a rod axis.

FIG. 14 shows a sectional view of the bone anchoring device with the locking ring in a second position.

FIG. 15 shows a sectional view of the bone anchoring device of FIG. 14, the section being taken along the longitudinal axis of the rod.

DETAILED DESCRIPTION

Figure 1:
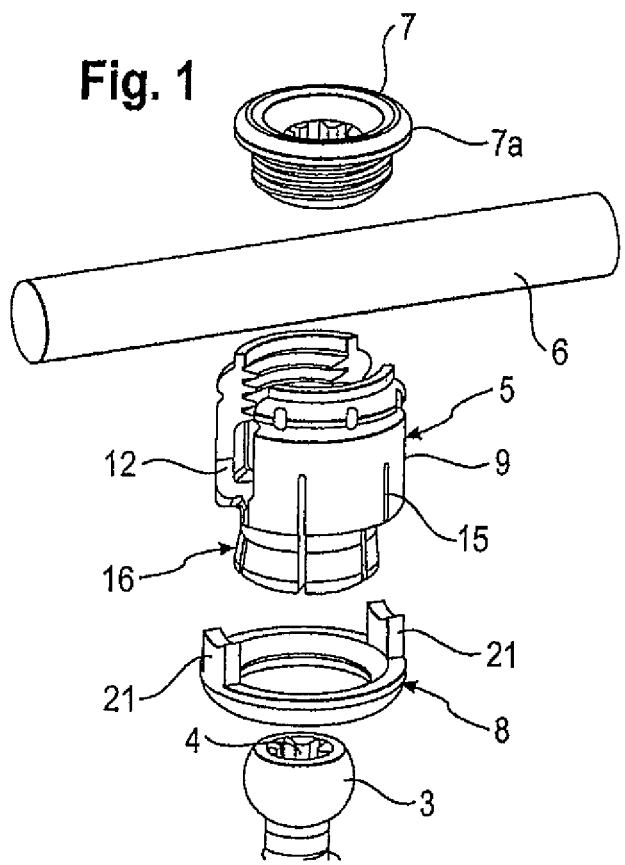
FIG. 1 shows a perspective exploded view of a first embodiment of the bone anchoring device.
Figure 2:
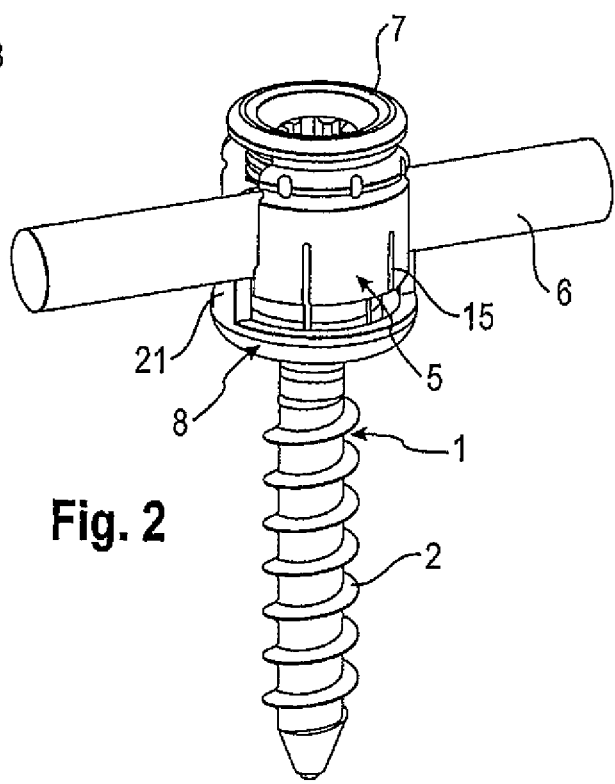
FIG. 2 shows a perspective view of the bone anchoring device of FIG. 1 in an assembled state.
Figure 9:
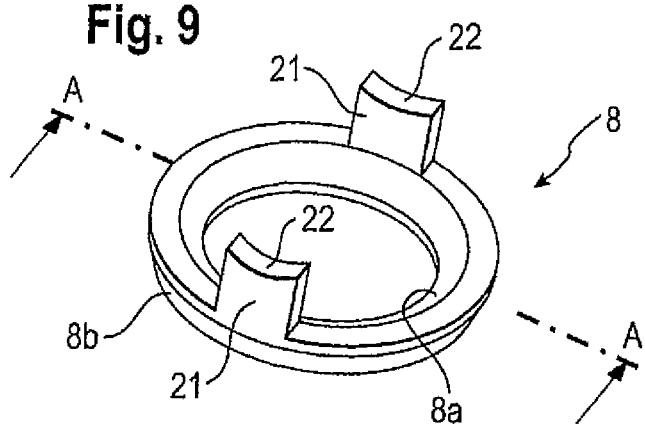
FIG. 9 shows a perspective view of the locking ring of the receiving part according to the first embodiment.
Figure 10:
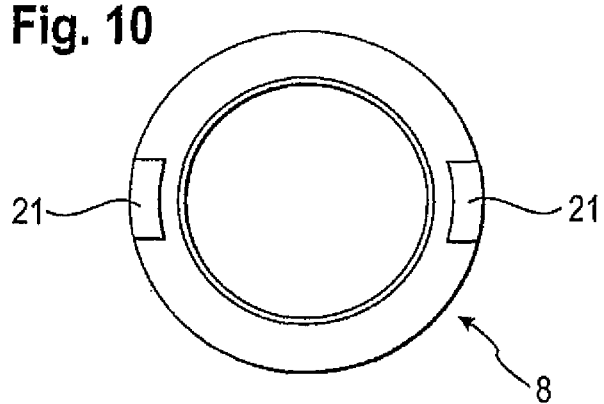
FIG. 10 shows a top view of the locking ring of FIG. 9.

As shown in FIGS. 1 and 2, the bone anchoring device according to a first embodiment includes a bone anchoring element 1 in the form of a bone screw having a threaded shaft 2 and a head 3 with a curved surface portion, in this embodiment a spherical segment-shaped head. The head 3 has a recess 4 for engagement with a screwing-in tool. The bone anchoring device further comprises a receiving part body 5 for receiving a rod 6 to connect it to the bone anchoring element 1. Further, a closure element 7 in the form of an inner screw is provided for securing the rod 6 in the receiving part body 5. In addition, the bone anchoring device comprises a locking ring 8 for locking the head 3 in the receiving part body 5.

As can be seen in particular in FIGS. 3 to 8, the receiving part body 5 comprises a rod receiving portion 9 which is substantially cylindrical and which has a first end 9a and opposite second end 9b. The rod receiving portion 9 has a coaxial first bore 10 provided at the second end 9b. The diameter of the first bore 10 is smaller than the diameter of the head 3 of the bone anchoring element. The rod receiving portion 9 also comprises a coaxial second bore 11 extending from the first end 9a to a distance from the second end 9b. The diameter of the second bore 11 is larger than that of the first bore 10 and larger than the diameter of the rod 6. A substantially U-shaped recess 12 is provided in the rod receiving portion 9 which extends from the first end 9a towards the second end 9b, the diameter of the recess 12 being slightly larger than the diameter of the rod 6 in such a way that the rod 6 can be placed in the recess 12 and can be guided therein. The recess 12 forms two free legs 12a, 12b on which an internal thread 13 is provided. The internal thread can be a metric thread, a flat thread, a negative angle thread, a saw-tooth thread or any other thread type. Preferably, a thread form such as a flat thread or negative angle thread is used, which prevents splaying of the legs 12a, 12b when the inner screw 7 is screwed-in. The depth of the recess 12 is such that the rod 6 and the inner screw 7 can be inserted between the legs. Between the bottom of the recess 12 and each of the legs 12a, 12b, a flat section 14 is provided forming the end of the bore 11.

As can be seen in FIGS. 1, 3 and 8, cuts 24 are provided in the rod receiving portion 9 on either end of the channel formed by the recess 12.

The rod receiving portion 9 of the receiving part body 5 further comprises a plurality of coaxial slits 15 extending from the second end 9b to a distance from the first end, wherein the distance corresponds approximately to the length of the internal thread 13. The slits 15 are open at the second end 9b and extend, as can be seen in particular in FIGS. 3, 7 and 8 through the flat section 14 towards the substantially U-shaped recess 12. At least one slit 15, and preferably more than one slit, is provided on either side of the recess 12. The number of slits is selected according to the degree of flexibility to be provided by the slits. This may depend on the material and the wall thickness and/or other factors.

Adjacent to the second end 9b, the receiving part body 5 comprises a head receiving portion 16 providing an accommodation space for the head 3 of the bone anchoring element 5. The head receiving portion 16 has a tapered outer surface which tapers towards the second end 9b and which has an open end 17 opposite to the second end 9b. The exterior surface of the head receiving portion 16 can be partially or fully tapered. It is tapered at least in the region of the largest diameter of the accommodation space for the head 3. The open end 17 can have a rounded edge. As can be seen in particular in FIG. 4, the outer diameter of the rod receiving portion 9 at its second end 9b is larger than the outer diameter of the head receiving portion 16 adjacent to the second end 9b and is also larger than the outer diameter of the head receiving portion at the open end 17. Hence, the head receiving portion 16 is recessed with respect to the rod receiving portion 9.

As can be seen in particular in FIGS. 13 to 15, the head receiving portion 16 has an internal hollow section 18 forming a seat for the head 3 of the bone anchoring element 1. The hollow section 18 is adapted in its shape to the shape of the head 3, in the embodiment shown, the hollow section 18 is a spherical section to accommodate the spherical head 3. The hollow section 18 is dimensioned in such a way that it encompasses the head 3 of the bone anchoring element from the side, covering a region including the largest diameter of the head 3.

As can be seen in particular in FIGS. 3 to 8, a plurality of slits 19 are provided in the head receiving portion 16 which are open to the open end 17 and extend from the open end 17 to the second end 9b of the rod receiving portion and which may continue as the slits 15 of the rod receiving portion 9, thereby forming continuous slits extending from the open end 17 of the head receiving portion into the rod receiving portion 9. The number of slits 19 may be equal to the number of slits 15, however, it can be smaller or larger depending on the desired flexibility of the head receiving portion 16. In addition slits 20 may be provided on the side of the head receiving portion 16 which are aligned with the substantially U-shaped recess 12 of the rod receiving portion, as shown in FIG. 6. The slits 20 end at a distance from the second end 9b. The flexibility of the head receiving portion 16 is such that the head 3 of the anchoring element can be inserted by expanding the head receiving portion and can be clamped by compressing the head receiving portion. The slits 15 in the rod receiving portion facilitate mounting of the receiving part body 5 onto the head 3 manually, for example, at any time before or during surgery.

The locking ring 8 will now be described with reference to FIGS. 1 and 9 to 12. At least a portion of the locking ring 8 has a substantially cylindrical outer surface with an outer diameter corresponding substantially to the outer diameter of the rod receiving portion 9 of the receiving part body 5. The height of the locking ring 8 in an axial direction is smaller than that of the head receiving portion 16 of the receiving part body 5, so that, as shown in FIGS. 2 and 14, there is a distance between the locking ring 8 and the second end 9b of the receiving part 5 when the locking ring 8 is in a second position $P_2$ in which the head 3 is locked.

Figure 11:
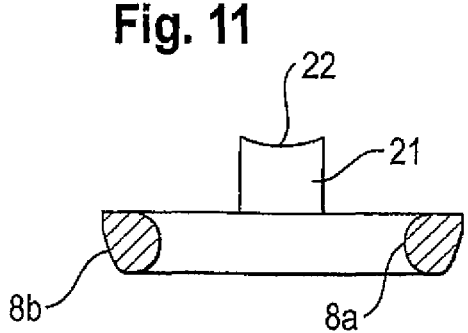
FIG. 11 shows a sectional view of the locking ring of FIG. 9 along line A-A.
Figure 12:
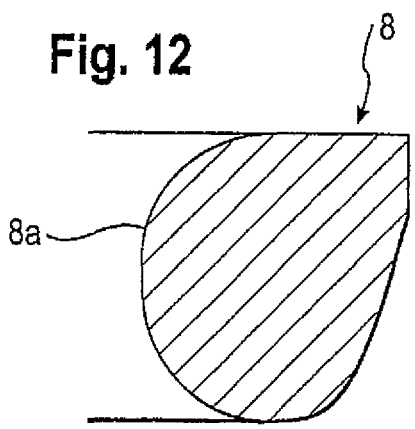
FIG. 12 shows an enlarged detailed view of a portion of the sectional view of FIG. 11.

As particularly shown in FIGS. 11 and 12, the locking ring 8 has on its inner side a curved interior surface portion 8a. The curvature is directed to the center of the locking ring. The curved interior surface portion 8a can have a spherical curvature. Other types of curvatures are also possible. The radius of the curvature is smaller than the radius of the head 3. The dimensions of the locking ring with respect to its inner portions are such that the locking ring 8 can slide along the outer surface of the head receiving portion 16 thereby compressing the head receiving portion 16 increasingly as the locking ring 8 slides downward.

As can be seen in particular in FIGS. 1, 2 and 9 to 11, the locking ring 8 further comprises on its side facing the second end 9b two projections 21 located diametrically opposite to each other. The projections 21 have such a height that they project above the bottom of the substantially U-shaped recess 12 and extend into the cuts 24 when the locking ring 8 is in a position in which the head 3 is not yet clamped. The free end 22 of the projections 21 can be curved, particularly inwardly curved, with a curvature corresponding to a curvature of the rod 6. The locking ring is arranged in such a way around the head receiving portion 16 of the receiving part body 5 that the projections are located at the positions of the recess 12. By means of this, the projections 21 which project into the recess 12 prevent or minimize occurrence of the locking ring 8 from rotating when the rod 6 is not inserted.

The flexibility of the head receiving portion 16 and the size of the head receiving portion at the open end 17 allows the locking ring 8 to be mounted by assembling it from the free end 17 onto the head receiving portion 16. Since the outer diameter of the head receiving portion 16 is smaller than that of the rod receiving portion 9, the locking ring does not project or only minimally projects beyond the rod receiving portion in a radial direction. The locking ring 8 may have a tapered exterior surface portion 8b as shown in FIG. 11 to further reduce its diameter towards the direction of the open end 17.

When the rod is not yet inserted or not pressed into the recess 12, the locking ring is movable between a first position $P_1$ as shown in FIG. 13 limited by the second end 9b of the rod receiving part which acts as a stop and a second position $P_2$ near the open end 17 of the head receiving portion as shown in FIG. 14 which is defined by the locking of the head 3 by means of compression of the head receiving portion 16. The tapered exterior surface of the head receiving portion prevents or reduces dislodging of the locking ring 8 in the direction of the open end 17.

The inner screw 7 has a thread corresponding to the internal thread 13 provided on the legs. If a thread form which prevents the legs from splaying is used, a single closure element such as the inner screw 7 is sufficient. This reduces the size of the bone anchoring device in a radial direction. As shown in particular in FIG. 1, the inner screw 7 may have on its side opposite to the rod 6 a rim 7a which can act as a stop for screwing in the inner screw. Also, the rim 7a facilitates gripping.

The receiving part body 5, the locking ring 8, the inner screw 7 and the bone anchoring element 1 may be made of a bio-compatible material, for example, of titanium or stainless steel, or a bio-compatible alloy or bio-compatible plastic material with sufficient strength.

The bone anchoring device may be preassembled with the locking ring 8 mounted on the head receiving portion 16 of the receiving part body 5 from the open end 17. Alternatively, the bone anchoring element 1 can also be preassembled with the receiving part 5 and the locking ring 8.

The locking of the head 3 is now explained with respect to FIGS. 13 to 16. When the locking ring 8 is in its first position $P_1$ near the second end 9b of the rod receiving portion, the locking ring 8 does not compress the head receiving portion. The curved portion 8a does not or does only minimally contact the exterior surface portion of the head receiving portion as shown in FIG. 13. The rod 6 is not yet pressed down by the tightening of the inner screw 7. In this condition, the head 3 of the bone anchoring element is fully pivotable within the hollow portion 18.

When the inner screw is tightened, it presses onto the rod 6 which presses onto the locking ring 8 via the projections 21. In the course of tightening the inner screw 7 the locking ring 8 is shifted downward until the curved portion 8a engages the tapered exterior surface portion of the head receiving portion 16. When the locking ring is at a position of the greatest diameter of the head 3 in a direction of the central axis A of the bone anchoring device, the pressure exerted by the curved portion 8a of the locking ring onto the head receiving portion 3 is largest as shown by the arrows in FIG. 16, whereby the head 3 is clamped in such a way that it is locked. Simultaneously, a further downward movement of the locking ring 8 is prevented as shown in FIGS. 14 and 16.

Figure 17:
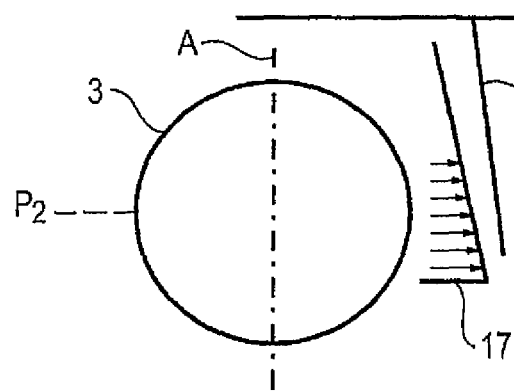
FIG. 17 shows for comparison a schematic view of the locking principle of bone anchoring devices with engaging tapered surfaces in a first example.
Figure 18:
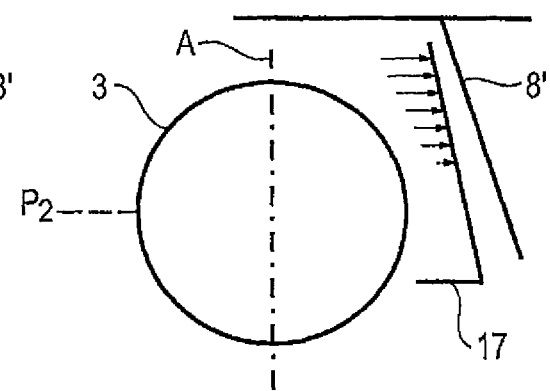
FIG. 18 shows for comparison a schematic view of the locking principle of engaging tapered surfaces in a second example.
Figure 19:
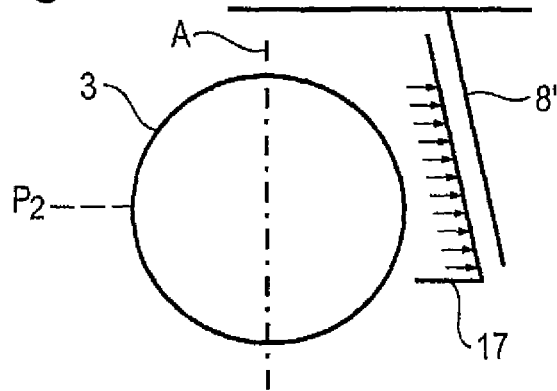
FIG. 19 shows for comparison a schematic view of the locking principle of engaging tapered surfaces in a third example.
Figure 20:
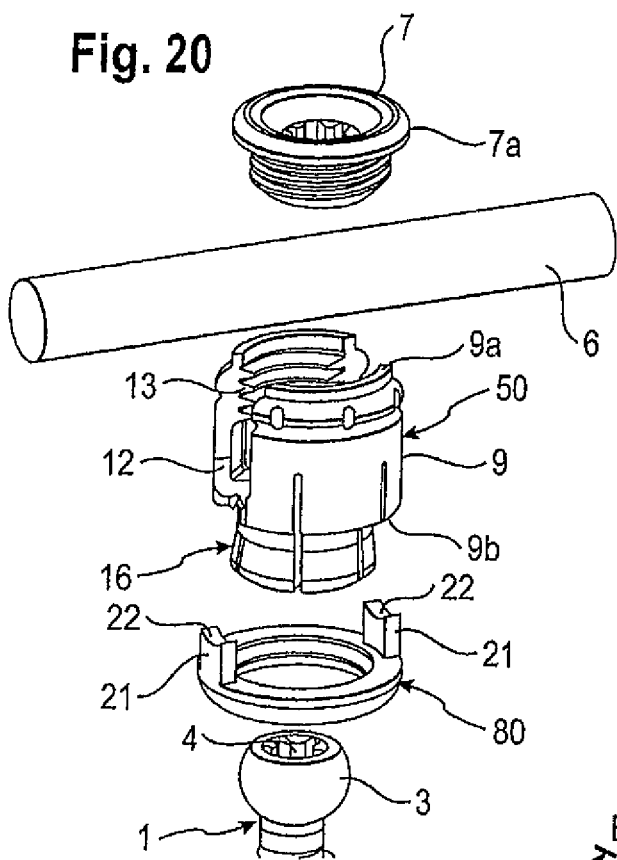
FIG. 20 shows a perspective exploded view of a second embodiment of the bone anchoring device.
Figure 21:
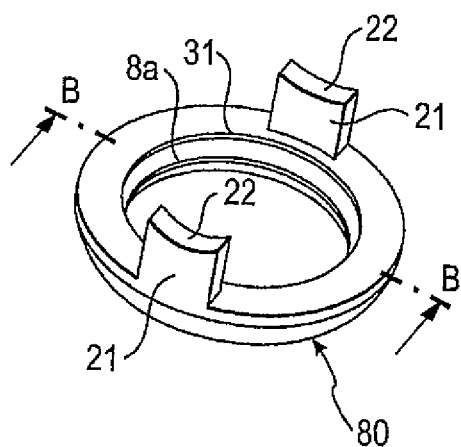
FIG. 21 shows a perspective view of the locking ring of the second embodiment.
Figure 22:
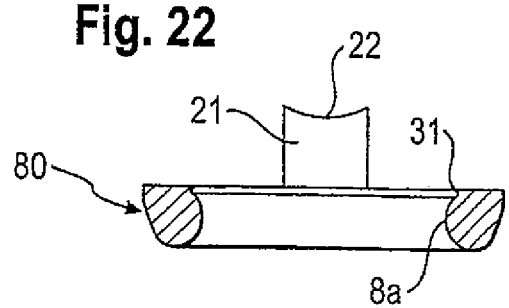
FIG. 22 shows a sectional view of the locking ring of FIG. 21 along line B-B.

FIGS. 17 and 18 show the force distributions indicated by arrows in cases where the locking ring has an internal tapered surface portion as known from the prior art. In FIG. 17 the locking ring 8' contacts the tapered exterior surface portion of the head receiving portion near the open end 17. As shown by the length of the arrows, the clamping force is largest near the open end 17 and not at the position $P_2$ of the largest diameter. In FIG. 18 the exterior tapered surface of the locking ring 8' contacts the tapered exterior surface portion of the head receiving portion above the position $P_2$ of the largest diameter, which also results in diminishing force towards the position with the largest diameter. In FIG. 19 the tapered surfaces of the head receiving portion and the locking ring 8' are parallel, which results instead in a uniform pressure distribution.

Figure 16:
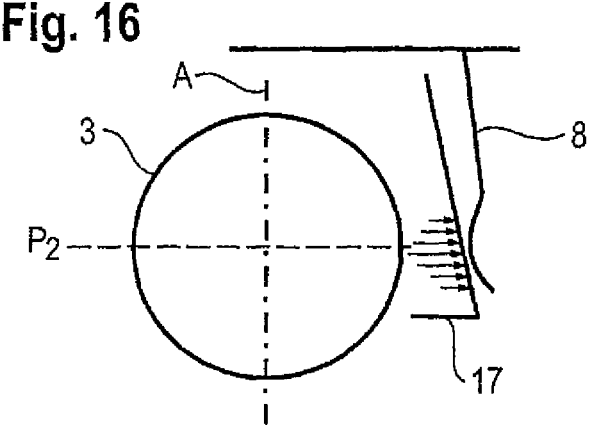
FIG. 16 shows a schematic view of the locking principle of the bone anchoring device according to an embodiment of the invention.

The pressure distribution of the locking ring exerted onto the head receiving portion according to an embodiment of the invention as shown in FIG. 16 has a maximum pressure at the position $P_2$ where the maximum diameter of the head 3 is located.

The bone anchoring device can be used in several ways. In one way of use the bone anchoring element, the receiving part body and the locking ring are preassembled. The bone anchoring element is screwed into the bone with the receiving part mounted to the anchoring element. The recess 4 of the head can be accessed with the screwing-in-tool through the first bore 10. The locking ring is in its first position close to the second end 9b where it does not clamp the head 3. The flexible receiving part creates a slight pretension having a small overlap on the inner curved surface of the hollow portion 18. In this state the head 3 is pivotably held in the second portion 16 which allows the receiving part body 5 to be safely aligned to receive the rod. Once the correct position of the rod with respect to other bone anchoring devices is achieved, the inner screw 7 is screwed between the legs until it presses onto the rod. The rod is moved towards the bottom of the substantially U-shaped recess thereby engaging the free ends 22 of the projections 21, respectively, and shifting down the locking ring 8. When the locking ring 8 is moved towards the free end 17 of the second portion, it radially compresses the second portion 16, thereby clamping the head. Since the force which is exerted by the locking ring acts with the interior curved surface 8a from the lateral side, the force necessary for safely immobilizing the head is smaller than in the case in which the force acts from above on the top of the head 3. It also reduces the size of the device by allowing the wall thickness of the receiving part to be reduced. Final tightening of the inner screw 7 locks the rod 6 and the head 3 simultaneously.

In another way of use, only the receiving part body 5 and the locking ring 8 are preassembled. The bone anchoring element 3 is first screwed into the bone, and then the receiving part is mounted onto the head 3 while the locking ring is in its first position close to the second end 9b and not compressing the second portion 16. Alternatively, the bone anchoring element 1 and the receiving part body with the preassembled locking ring are assembled by pressing the receiving part onto the head 3. This provides an opportunity to select an appropriate bone anchoring element in terms of diameter, length and other features of the anchoring section. Hence, a modular system can be provided, including different receiving parts and several bone anchoring elements, which then individually can be chosen and adapted.

In yet another way of use, the inner screw is tightened to lock the head and the rod. Thereafter, the inner screw is loosened to allow further adjustments of the rod. The head may remain temporarily clamped due to the frictional force which holds the locking ring in place.

FIGS. 20 to 26 show a second embodiment of a bone anchoring device. Portions and elements which are similar to the first embodiment are designated with the same reference numerals as in the description of the first embodiment, and the description thereof will not be repeated.

The second embodiment differs from the first embodiment with respect to the receiving part body and the locking ring. As shown in particular in FIGS. 25 and 26 the receiving part body 50 has on its face forming the second end 9b of the rod receiving portion an annular projection 30 projecting downwards which is arranged at a distance from the exterior surface of the head receiving portion adjacent to the second end 9b. The projection 30 has a curved exterior surface 30a forming a nose which cooperates with a groove and a projecting upper edge 31 at an upper portion of a curved portion 8a of a locking ring 80. The position and the size of the nose 30a and the edge 31 are such that a resilient engagement is possible which allows for temporary fixation of the locking ring 80 at its first position $P_1$ where the locking ring 80 is released upon exerting pressure with the rod.

Figure 23:
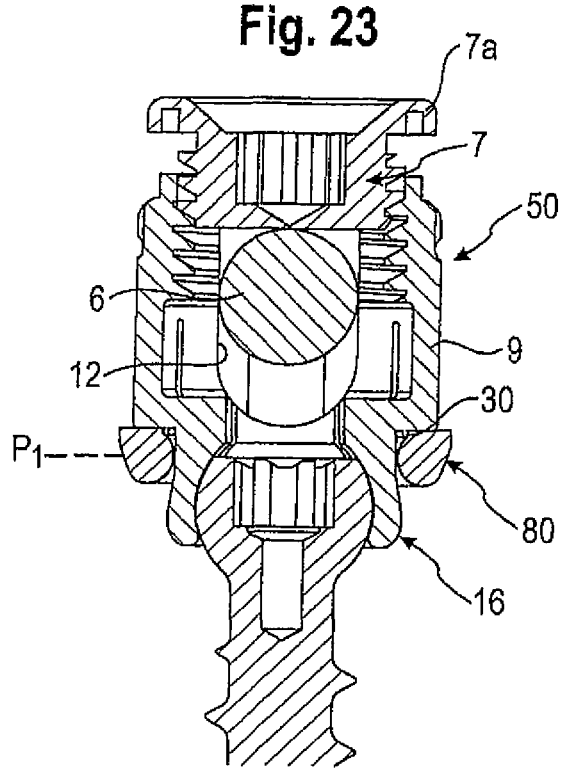
FIG. 23 shows a sectional view of the bone anchoring device of the second embodiment when the locking ring is in a first position, the section being taken perpendicular to a rod axis.
Figure 24:
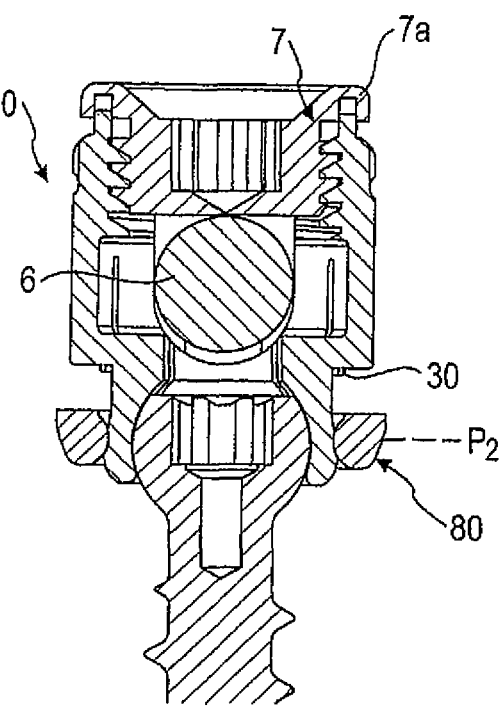
FIG. 24 shows a sectional view of the bone anchoring device of the second embodiment when the locking ring is in a second position, the section being taken perpendicular to the rod axis.
Figure 25:
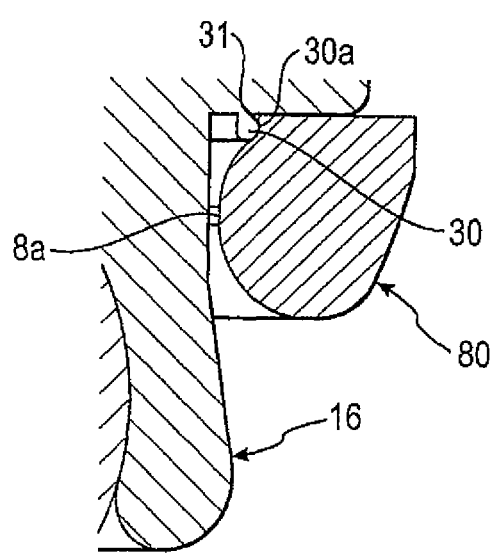
FIG. 25 shows an enlarged detailed view of a portion of FIG. 23.
Figure 26:
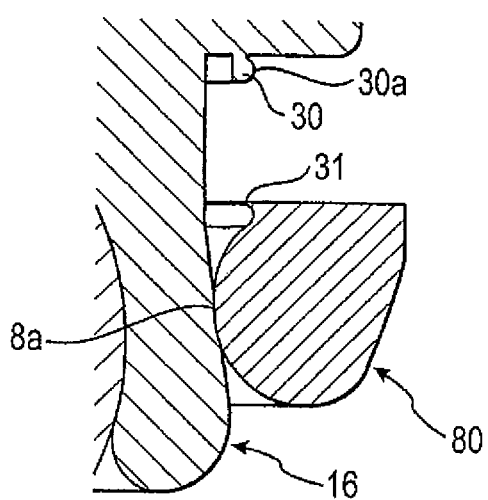
FIG. 26 shows an enlarged detailed view of a portion of FIG. 24.

As can be seen in FIG. 23, the locking ring 80 is in its upper position $P_1$ releaseably held by the engagement of the edge 31 with the nose 30a. As can be seen in FIGS. 25 and 26, pressing down of the rod leads to disengagement of the edge 31 and nose 30a, and the locking ring 80 can be moved into its second position $P_2$ where it locks the head.

Further modifications of the embodiments described are possible. For example, the head of the bone anchoring element can have any other shape, such as, for example, a cylindrical shape whereby a monoaxial bone screw is provided allowing rotation of the screw element with respect to the receiving part around a single axis. The head 3 can also be conically shaped or otherwise shaped and the internal hollow section 18 of the head receiving portion is adapted to this shape. In a further modification, the receiving part body 5, or at least the head receiving portion 16, are made of a biocompatible plastic material which provides elasticity to a certain degree. In this case, the slits may be omitted.

In other embodiments, the projections of the locking ring which engage the rod can have another shape. For example, the surface of the free end can be flat or otherwise shaped.

In other embodiments, the head receiving portion can have an inclined open end 17 to allow a greater angulation of the head in one direction.

While the present invention has been described in connection with certain exemplary embodiments, it is to be understood that the invention is not limited to the disclosed embodiments, but is instead intended to cover various modifications and equivalent arrangements included within the spirit and scope of the appended claims, and equivalents thereof.

What is claimed is:

1. A receiving part for receiving a rod for coupling the rod to a bone anchoring element, the receiving part comprising:
    a receiving part body comprising:
        a rod receiving portion with a channel for receiving a rod, and
        a head receiving portion for accommodating a head of a bone anchoring element, the head receiving portion having an open end and being flexible so as to allow introduction and clamping of the head and an exterior surface, wherein a longitudinal axis extends from the rod receiving portion to the head receiving portion; and
    a locking ring configured to be arranged around the head receiving portion and comprising an interior surface with a curved portion curving along a direction parallel to the longitudinal axis, wherein when the locking ring is around the head receiving portion, the locking ring is movable along the longitudinal axis between a first position wherein a space between the locking ring and the head receiving portion permits expansion of the head receiving portion for inserting the head, and a second position wherein the curved portion is configured to engage the exterior surface of the head receiving portion to clamp the head therein.

2. The receiving part of claim 1, wherein the curved portion of the locking ring has a convex curvature.

3. The receiving part of claim 1, wherein the head receiving portion defines an accommodation space for accommodating the head, and wherein a height of the locking ring is smaller than a height of the accommodation space.

4. The receiving part of claim 1, wherein in the first position the head receiving portion permits pivoting of the head, and wherein in the second position the head is clamped and locked in the head receiving portion.

5. The receiving part of claim 1, wherein the locking ring is releaseably held in the first position.

6. The receiving part of claim 5, wherein the rod receiving portion comprises a projection and the locking ring comprises a corresponding groove for receiving the projection when the locking ring is held in the first position.

7. The receiving part of claim 1, wherein the locking ring is configured to move when a pressure is exerted onto the locking ring via the rod.

8. The receiving part of claim 1, wherein the head comprises a curved outer surface and wherein a radius of curvature of the curved portion of the locking ring is smaller than a radius of curvature of the curved outer surface of the head.

9. The receiving part of claim 1, wherein the rod receiving portion comprises a first end and a second end, and a recess extends from the first end in a direction of the second end to form the channel.

10. The receiving part of claim 1, wherein the rod receiving portion comprises a first end and a second end, and the head receiving portion is at the second end, and wherein an outer diameter of the head receiving portion at the second end is smaller than a diameter of the rod receiving portion at the second end.

11. The receiving part of claim 1, wherein the head receiving portion includes a plurality of slits adjacent to the open end.

12. The receiving part of claim 1, wherein the rod receiving portion comprises a first end and a second end, and the head receiving portion is at the second end, and wherein the rod receiving portion comprises a plurality of slits extending from the second end to a distance from the first end.

13. The receiving part of claim 1, wherein the receiving part body comprises at least one continuous slit extending continuously from the open end of the head receiving portion and into the rod receiving portion.

14. The receiving part of claim 1, wherein the head receiving portion is configured to be compressed by the locking ring.

15. The receiving part of claim 1, wherein a pressure distribution exerted by the looking ring onto the head receiving portion is greatest at a location approximate a maximum diameter of the head.

16. The receiving part of claim 1, wherein the curved portion extends continuously from a first end of the interior surface to a second end of the interior surface opposite the first end.

17. A bone anchoring device comprising:
    a bone anchoring element comprising a head and a threaded shaft; and
    a receiving part for receiving a rod for coupling the rod to the bone anchoring element, the receiving part comprising:
        a receiving part body comprising a rod receiving portion with a channel for receiving the rod, and a head receiving portion for accommodating the head of the bone anchoring element, the head receiving portion having an open end and being flexible so as to allow introduction and clamping of the head and an exterior surface, wherein a longitudinal axis extends from the rod receiving portion to the head receiving portion; and
        a locking ring configured to be arranged around the head receiving portion and comprising an interior surface with a curved portion curving along a direction parallel to the longitudinal axis, wherein when the locking ring is around the head receiving portion, the locking ring is movable along the longitudinal axis between a first position wherein a space between the locking ring and the head receiving portion permits expansion of the head receiving portion for inserting the head, and a second position wherein the curved portion is configured to engage the exterior surface of the head receiving portion to clamp the head therein.

18. The bone anchoring device according to claim 17, further comprising:
   the rod; and
   a closure element for securing the rod in the channel.

19. The bone anchoring device according to claim 18, wherein the closure element comprises an inner screw.

20. A method of coupling a rod to a bone anchoring element via a receiving part, the receiving part comprising a rod receiving portion with a channel for receiving the rod and a head receiving portion for accommodating a head of the bone anchoring element, the head receiving portion having an open end and being flexible so as to allow introduction and clamping of the head and an exterior surface, wherein a longitudinal axis extends for the rod receiving portion to the head receiving portion, and a locking ring around the head receiving portion and comprising an interior surface with a curved portion curving along a direction parallel to the longitudinal axis, wherein the locking ring is movable along the longitudinal axis between a first position wherein a space between the locking ring and the head receiving portion permits expansion of the head receiving portion for inserting the head, and a second position wherein the curved portion is configured to engage the exterior surface of the head receiving portion to lock a position of the bone anchoring element relative to the receiving part, the method comprising:
   introducing the head of the bone anchoring element into the open end of the head receiving portion when the locking ring is in the first position;
   pivoting the head relative to the head receiving portion to be aligned with the rod;
   inserting the rod in the channel of the rod receiving portion;
   advancing a closure element in the channel to push the rod against the locking ring; and
   further advancing the closure element in the channel towards the head receiving portion to force the locking ring towards the open end of the head receiving portion to the second position via the rod and to lock a position of the rod relative to the receiving part,
wherein advancement of the locking ring towards the open end of the head receiving portion to the second position engages the curved portion of the locking ring with the exterior surface of the head receiving portion to compress the head receiving portion and to lock the position of the bone anchoring element relative to the receiving part.

* * * * *